(12) United States Patent
Le Gallou et al.

(10) Patent No.: US 10,120,207 B2
(45) Date of Patent: Nov. 6, 2018

(54) METHOD FOR DETERMINING OCULAR AND OPTICAL MEASUREMENTS

(71) Applicant: FITTINGBOX, Labege (FR)

(72) Inventors: Sylvain Le Gallou, Baziege (FR); Ariel Choukroun, Toulouse (FR)

(73) Assignee: FITTINGBOX, Labege (FR)

( * ) Notice: Subject to any disclaimer, the term of this patent is extended or adjusted under 35 U.S.C. 154(b) by 0 days.

(21) Appl. No.: 14/348,044

(22) PCT Filed: Sep. 27, 2012

(86) PCT No.: PCT/EP2012/069044
§ 371 (c)(1),
(2) Date: Mar. 27, 2014

(87) PCT Pub. No.: WO2013/045531
PCT Pub. Date: Apr. 4, 2013

(65) Prior Publication Data
US 2014/0253875 A1    Sep. 11, 2014

(30) Foreign Application Priority Data

Sep. 29, 2011   (FR) ...................................... 11 02952
Nov. 18, 2011   (FR) ...................................... 11 60547

(51) Int. Cl.
| | | |
|---|---|---|
| A61B 3/10 | (2006.01) | |
| A61B 3/14 | (2006.01) | |
| A61B 3/02 | (2006.01) | |
| A61B 3/00 | (2006.01) | |
| G02C 13/00 | (2006.01) | |
| A61B 3/11 | (2006.01) | |

(52) U.S. Cl.
CPC .......... *G02C 13/005* (2013.01); *G02C 13/003* (2013.01); *A61B 3/111* (2013.01)

(58) Field of Classification Search
CPC .......... A61H 5/00; G02C 13/005; G02C 9/00; G02C 5/00; G02C 11/02; G02C 1/02; G02C 5/006; A61B 3/103; A61B 3/14; A61B 3/113; A61B 3/1208; A61B 3/1225; A61B 3/024; A61B 3/032; A61B 3/1015
USPC .......... 351/204, 200, 203, 159.74, 205, 206, 351/209, 210, 220–223, 227–231, 246, 351/47, 41, 52, 57, 110, 116, 159, 177
See application file for complete search history.

(56) References Cited

U.S. PATENT DOCUMENTS

| | | | |
|---|---|---|---|
| 2005/0073648 A1* | 4/2005 | Toshima et al. ............... | 351/200 |
| 2007/0279590 A1 | 12/2007 | Ebisawa | |
| 2008/0192990 A1* | 8/2008 | Kozakaya .......... | G06K 9/00221 382/117 |
| 2009/0109400 A1 | 4/2009 | Yoshinaga | |
| 2009/0304232 A1* | 12/2009 | Tsukizawa ............. | A61B 3/113 382/103 |
| 2010/0128220 A1 | 5/2010 | Chauveau | |
| 2010/0195045 A1 | 8/2010 | Nauche et al. | |

(Continued)

*Primary Examiner* — Dawayne A Pinkney
(74) *Attorney, Agent, or Firm* — Im IP Law; C. Andrew Im

(57) ABSTRACT

A method for determining ocular and optical measurements for the production and fitting of corrective eyeglasses for a user with the aid of the a camera. The method utilizes a protocol for reconstructing the system of the user's eyes in three dimensions by modeling the system of the eye, thereby providing precise ocular and optical measurements. The method uses test objects that are connected or not connected to the user's face.

21 Claims, 5 Drawing Sheets

(56) References Cited

U.S. PATENT DOCUMENTS

| | | | | |
|---|---|---|---|---|
| 2011/0267578 A1* | 11/2011 | Wilson | ................... | A61B 3/111 |
| | | | | 351/204 |
| 2013/0076884 A1* | 3/2013 | Choukroun | ............ | A61B 3/111 |
| | | | | 348/78 |
| 2015/0309338 A1* | 10/2015 | Chauveau | ................ | G02C 7/02 |
| | | | | 351/204 |

* cited by examiner

METHOD FOR DETERMINING OCULAR AND OPTICAL MEASUREMENTS

RELATED APPLICATIONS

This application is a § 371 application from PCT/EP2012/069044 filed Sep 27, 2012, which claims priority from French Patent Application No. 1102952filed Sep 29, 2011 and French Patent Application No. 1160547filed Nov 18, 2011, each of which is herein incorporated by reference in its entirety

TECHNICAL FIELD OF THE INVENTION

The present invention relates to the field of ocular and optical measurements, and more particularly a method for determining ocular and optical measurements.

BACKGROUND OF THE INVENTION

The purpose of ocular and optical measurements is the mounting of lenses on frames that are worn. The mounting of lenses must provide an ideal correction as well as comfort of vision for the usual everyday activities (driving, reading etc.) which each represent different conditions of accommodation and position of the eye with respect to the lens. Several measurements are necessary for the fabrication and mounting of the lens.

Currently the quantities used are those of activities in far-vision, which correspond to a focus at infinity (>2 m), and in near vision (>30 cm and <2 m) and the following measurements:

measurement for single correction vision (or SV for Single Vision) for unifocal lenses:
   Pupillary Distance (PD): the pupillary distance is the distance between the centers of the pupils when the subject focuses at infinity. This measurement relates to the eye system only.
measurements for strong and/or progressive correction vision (PV for Progressive Vision) for varifocal or progressive lenses: these measurements have the purpose of enabling the precise mounting of the lens by considering the frame that is worn. They therefore relate to the adjustment of the vision for a frame that is worn and adjusted for the face, by considering a focus at infinity perfectly aligned with the direction of the face.
   Monopupillary distance (MonoPD): distance between the projection of the pupil in the plane of the lens and the center of the frame. This quantity measures the horizontal off-centering to be applied during the edging of the lens.
   Heights (Segment Heights): distance between the projection of the pupil in the plane of the lens and the bottom of the frame (presumed inside of the inner bezel). This quantity measures the vertical off-centering to be applied during the edging of the lens.

These measurements correspond to a sight of the eye at infinity. Near vision can be measured for distances considered to be fixed (40 cm), and they are generally deduced from tables.

In practice, the eye is placed in a situation of sight and tools make it possible to measure the place where the ray sighted by the eye intersects the lens. This makes it possible to implicitly take account of the sighting parameters of the subject: slight strabismus, capacity of convergence, of accommodation, and leading eye as a function of the position and orientation with respect to the point sighted in binocular vision.

As a function of the correction, the lenses are cut to manage sighting shifts due to the lens itself. For this, the lens-eye distance and the lens-eye angle in infinity focus configuration for a neutral head hold are taken into account. Here again nomograms are considered, with an average lens-eye distance of 13 mm and an average angle, called pantoscopic angle, of 10 degrees.

However, if these defects are significant, the measurement of near vision becomes necessary, while taking account of the sighting situation: reading, working on a computer etc., so many situations that have different sighting heights with respect to the face and that vary with the habits of the person.

Currently, the fabrication of high-tech lenses makes it possible to adapt vision at various angles and distances of sight. Each eye being different, and the measurement being defined to be carried out in the plane of the lens, it is therefore useful to have as many measurements as there are different sighting needs. In practice, the optician does not have time to take said measurements with conventional tools.

There are thus various sources of error which combine and add together during a mounting of lenses on a pair of spectacles:

The measurement error on the shapes of the frame: in general, the optician puts the pair in a machine that feels the inner bezel of the frame: error +−0.2 mm. For rimless frames, the size of the demonstration lens is measured or the optician chooses the shape with his or her client.
   The lens edging error: the NF EN ISO 21987 standard gives maximum error values. Best practice production guides for opticians recommend in practice a maximum error of 1.5 mm for the error between the requested and the achieved horizontal centering, and of 1 mm maximum between the requested and the achieved vertical centering for progressive lenses.
   The interpupillary measurement error: error committed on the PD, monoPD and height. No official recommendation, but practical values obtained in the order of the half-millimeter for the PD, and of the millimeter per eye for the monoPD and heights.

There exist tables of maximum recommended errors on the final mounting as a function of the degree of correction and lens type. By subtraction, it can be deduced therefrom that the current interpupillary measurement qualities are adequate. But for this it is necessary that the measurements be performed correctly.

OBJECT AND SUMMARY OF TH INVENTION

The subject of the present invention is therefore to palliate one or more of the drawbacks of the prior art by proposing a method for determining ocular and optical measurements for the fabrication and mounting of lenses of corrective spectacles enabling more precise measurements.

To do this, the present invention proposes a method for determining ocular and optical measurements for the fabrication and mounting of lenses of corrective spectacles for a user, assisted by a camera, using a protocol of three-dimensional reconstruction of the eye system of the user by modeling the eye system.

The invention thus makes it possible to define lenses adapted to the eye of the user in a very simple manner, assisted by a camera. The set of measurements is taken directly at the same time.

According to one embodiment of the invention, the protocol comprises at least one step consisting in carrying out the ocular and optical measurements for various points of sight and various orientations of the face of the user.

According to one embodiment of the invention, the points of sight are three in number and the orientations of the face of the user are three in number.

According to one embodiment of the invention, the modeling is performed based on real quantities of the eye which are: the size of the iris, the size of the eyeballs, the orientation of the eyeballs in their socket, and the pose of the set of two eyes in a reference frame of the camera.

According to one embodiment of the invention, the method comprises a step of measuring the interpupillary distance (PD3D) between the two eyes reconstructed in three dimensions.

According to one embodiment of the invention, the method comprises a step of measuring the monopupillary distance (monoPD), the heights and the pantoscopic angle, directly in the three-dimensional system of the reconstructed eye.

According to one embodiment of the invention, the method comprises a step of aligning the image indices.

According to one embodiment of the invention, the method uses test objects securely fastened or not securely fastened to the face of the user.

According to one embodiment of the invention, the test object has the shape of a rectangular card.

According to one embodiment of the invention, the test object is contained in a visualization screen.

According to one embodiment of the invention, the determination of the metric size of the screen is done using a planar object.

According to one embodiment of the invention, the test object is used at the start of the protocol.

According to one embodiment of the invention, the face of the user acts as a test object for the eye system.

According to one embodiment of the invention, the method comprises a step of PV measurements with a virtual try-on of three-dimensional spectacles.

According to one embodiment of the invention, the method comprises a step of calibration and metric definition of the camera.

According to one embodiment of the invention, the method comprises a step of geometrical calibration of the screen.

According to one embodiment of the invention, the method includes a step of evaluating the stability and performance, which makes it possible to detect production defects and correct them.

According to one embodiment of the invention, the method is interactive and in real time.

According to one embodiment of the invention, the method is automatic.

According to one embodiment of the invention, the method comprises a step of analysis of the ocular behavior.

According to one embodiment of the invention, the method has a Client-Server architecture.

According to one embodiment of the invention, the method operates with two cameras connected by a known or unknown rigid stress.

According to one embodiment of the invention, the method operates with at least one device giving depth.

BRIEF DESCRIPTION OF THE DRAWINGS

Other features and advantages of the invention will be better understood and will become more clearly apparent on reading the description given below with reference to the appended figures given by way of example.

DETAILED DESCRIPTION OF AN EMBODIMENT OF THE INVENTION

Figure 1:
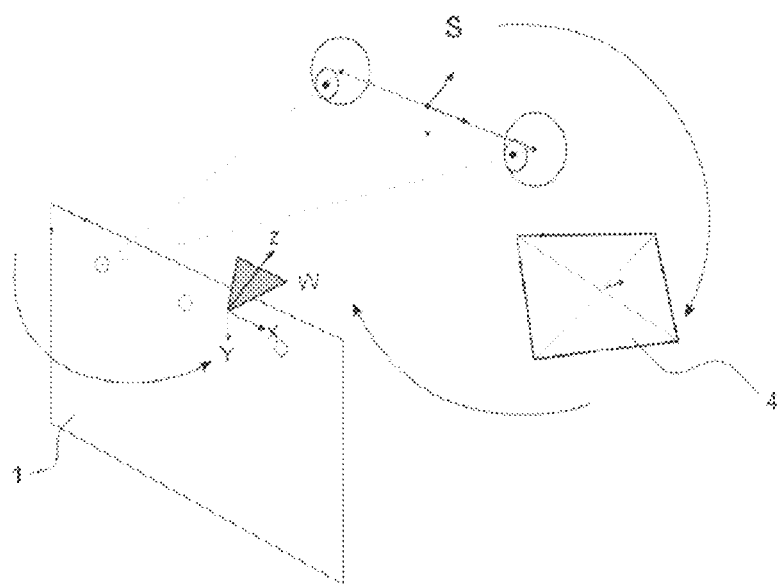
FIG. 1 is a schematic representation of a view in the space of a 3D reconstruction system.

The general context of the invention is that of the determination, by means of a standard definition video camera, of ocular and optical measurements enabling the fabrication and precise mounting of corrective lenses on a frame of spectacles. Two contexts of implementation are envisioned, the in-store context, which corresponds to the installation of a specific item of hardware at an optician's, and the online context, which corresponds to the use of standard item of hardware by any user connected to the internet.

A distinction is also made between two sets of measurements to be determined, as a function of the type of correction desired. So-called single correction (SV) corresponds to the fabrication and mounting of lenses correcting the same defects of vision over their whole surface. So-called progressive correction (PV) corresponds to the fabrication and mounting of lenses correcting different types of defects on different points of their surface ("progressive" lenses.)

These four contexts have in common the use of a single camera of any definition and of a non-specific luminous environment.

The system proposed by the invention makes it possible to obtain the measurements:
  opupillary distance (PD): the pupillary distance is the distance between the centers of the pupils when the subject focuses at infinity. This measurement relates to the eye system only.
  of monoPupillary distance (MonoPD): distance between the projection of the pupil in the plane of the lens and the center of the frame. This quantity measures the horizontal off-centering to be applied during the edging of the lens.
  of heights (Segment Heights): distance between the projection of the pupil in the plane of the lens and the bottom of the frame (presumed inside of the inner bezel). This quantity measures the vertical off-centering to be applied during the edging of the lens.
  pantoscopic angle, and
  all the measurements necessary for the mounting of the lenses that can result from the wearing of the spectacles and the expected sight, with a precision greater than that of the known systems in this field, as well as maximum accessibility.

For an ocular measurement system the precision is defined by three values: precision, stability and repeatability of the tool. The final precision in real conditions is the capability of the system to attain the precision during measurement.

Precision: this is the maximum offset with respect to the real value for a large majority of measurements. The precision describes the bias committed by the measuring instrument. This is the useful measurement for the edging of the lenses for example, as it is enough to measure the shape and the distances achieved by comparison with the expected data. The final precision in real conditions is the capacity of the system to attain the precision during measurement.

Stability: this is the maximum offset about the real value for measurements outside the precision range. Stability measures the influence of errors. This measurement corresponds to the capacity of the instrument to guarantee precision in various situations (individuals, experimental environment, etc.). The measurement system and its associated protocol must guarantee that the precision is attained in a certain percentage of cases, ideally very high. This measurement also expresses the capacity of the tool to avoid gross errors. Depending on the protocol of the tool, it is possible to define a new law of precision for the stability. Then the severity and implications of this type of error are evaluated as a function of the observed magnitude.

Repeatability: this is the number of unit measurements necessary to guarantee precision. It is no longer a case of the maximum error but of the average observed error by repeating the measurement a great number of times (asymptotic convergence). In practice, this gives an indication of the reliability of only carrying out the measurement with the instrument once, or of having to verify it several times.

In order to avoid having to redefine the pupillary distance PD for each angle of sight, this quantity is redefined independently of this parameter, and it is called PD3D. PD3D is the distance between the centers of rotation of the two eyes.

This definition relies on the fact that the point of formation of the image (optical center) of each eye is merged with its center of rotation ([Optometry product Guide, Zeiss], [Ophthalmic lenses and dispensing, Butterworth-Heinemann Optician, 1999 ISBN0750641584]). Other definitions exist, as a function of where the image formation zone is considered, but most come down to measuring points close to 0.1 mm. This measurement corresponds to the measurement of the pupillary distance PD at infinity, in the absence of strabismus. However, the benefit of this measurement is that it makes it possible to measure the pupillary distances PD at the desired angle when observing a subject focusing as a close to infinity as possible.

The measurements monoPD, Heights are redefined with the 3D point proposed being used for a reference frame. The edging of the varifocal lens will then be computed as a function of the position and orientation of the frame, and of the most frequent sight activities of the subject. A lens edged for measurements at infinity will correspond to the measurements used currently.

The system is composed of a central unit, of any webcam connected to this unit, of a conventional visualization screen, and of a test object. For certain measurements and according to certain configurations, the frame can be used for taking certain measurements. The hardware medium can take the form of a desktop or laptop PC, but also of tablets or mobile platforms (telephones.) The computation unit can be distributed over several media and certain remote computations if the user platform is connected to the Internet.

The software enabling the acquisition and computations can take the form of an application and/or an Internet site for a browser. Finally, the test object can take various shapes and sizes. The proposed test object is a standard object which enables anybody to access the measurement taking system without particular hardware, anywhere in the world. The features of the test object mean that the system proposed by the invention is non-invasive, or less invasive than current systems. On the other hand, this test object does not need to be attached to the frame of the spectacles.

Finally, the use protocol is very simple to understand by any user, which facilitates the accessibility of the invention. Contrary to existing systems, the measurement is taken automatically without an external qualified operator having to be involved to allow the protocol to be completed, which is the case in all the existing systems, and poses the risk of poor application of the protocol and of poor repeatability of the result.

The invention makes it possible to use any existing hardware on the market, and to guarantee the desired precision for images acquired with webcams in variable shooting conditions: ambient light, camera noise, resolution, image compression, change of colors, etc. The use of standard and widespread hardware allows the use of the method according to the invention at home as well as in stores. The protocol guarantees precise results, including for low-resolution images (from 640 pixels×480 pixels). The super-resolution attained depends on the principle of alignment of the image indices, and on its use with the global three-dimensional (3D) resolution.

The invention differs from current systems which rely on the transfer of the measurement of a known length onto the measurement in a face-on image of the distance between the two eyes, as well as on the single transfer of the measurement of the distance between the pupils by considering them in a known 3D oriented plane. These two methods are imprecise, unstable, and dependent on a very good shooting hardware and on a perfect infinity focus, which is never the case in practice.

The model disclosed here reconstructs all the phenomena modeled in 3D, and is free from problems of quality, image resolution and test object size. An interpupillary distance is then defined between the two 3D eyes, defined in the reference document as being the distance between the centers of rotation of the eyeballs.

The monoPD, heights, and pantoscopic angle measurements are measured directly in the 3D space metrically reconstructed by considering the eye system, the face and the 3D spectacles.

The protocol associated with the method of resolution makes it possible to find the desired measurements whatever the defects of vision, the age, and the ability of the person to open his or her eyes, and its execution is very easy to assimilate. The method of resolution is based on the composition of various carriages of the head and directions of the focus.

Privileged protocol: the user turns his or her head while focusing on the various points presented on each row by the sight lines. The sight lines are not necessarily exactly on the point displayed on the screen. Here, three points of sight and several orientations of the face captured in motion.

Alternative protocol: with several points of sight (here 7) and 3 configurations of orientation of the face. This protocol can be used for the alternative modelling of resolution without a test object or known 3D point of the face.

Several types of test object are proposed, securely fastened to the face, but not necessarily in a constant position on the surface of the face over the course of the experiment. These objects can be small in size and can be planar, which constitutes a novelty and scientific progress. Thus, a compact-disc (CD) or a card with a rectangular credit card shape are functional test objects for the proposed system. Unlike all the methods that use a card, the latter establish a transfer of measurement in the space that gives rise to consequent errors.

The test object can also be any frame of which a 3D reconstruction has been carried out. The latter test objects have the advantage of giving the PV measurements in the same acquisition protocol.

Finally, a protocol and a resolution are proposed such that the test object is no longer on the face but contained in the visualization screen.

A variant solution is proposed in which the test object is used at the start, then the initial protocol described can be carried out without any object on the face. In a first protocol, the face is reconstructed in 3D and the metric is contributed by the test object. Secondly, the main protocol is carried out, and the face has become the test object for the eye system.

In the case where 3D points of the face are known as well as their metric relationships, then this face can be used as test object for the resolution of the PD and the PV measurements.

A metric reconstruction of the 3D scene viewed by a camera is only possible if the latter is calibrated. Our method does not require any particular camera, it adapts to each camera via a calibration step using one of the proposed test objects.

Once the 3D metric of the eye system and the test object is obtained, it is proposed to take the PV measurements by virtually placing the 3D model of the chosen pair of spectacles. The 3D representation of the virtual pair makes it possible to simulate its placing on the face of the user, and to take the 3D PV measurements once the placing has been carried out. This placing can be automatic or manual.

The system is stable and proposes a measurement of the confidence in the attained result, which makes it possible to detect production defects and correct them.

The method being interactive and in real time, the feedback on the performance is immediate and guiding is facilitated.

Determination of the Pupillary Distance (PD) in Single-Camera Context

The system according to the invention proposes the features of a reliable measurement system that guarantees the measurements of precision, stability and repeatability defined above.

The system makes it possible to measure all the quantities associated with definite focuses and orientations of the head. The system can thus enable just as many measurements adapted to the vision of the subject, the desired precision on the lenses and the vision activities being considered. In this respect the PD3D is considered as the primordial quantity, since it measures the mechanical stresses of the eye system by detaching itself from problems of vision and conditions of a contextual nature.

The quality of measurement is guaranteed by the possibility of calibrating the system when this is necessary, for monitoring.

The system is automated. Indeed, it is important that it be as automatic as possible in order to avoid any human error, which adds to the dependence on outside factors: fatigue, lack of training or experience, poor interpretation (of the image for example), etc. When manual intervention is necessary, the system must be able to monitor it and describe it.

The automation of the system also relates to the capacity to replay the experiment to carry out the measurement an adequate number of times and ensure the repeatability of each instance of the protocol.

The system proposes a functionality of evaluation of its state, by automatic actions or easily implementable monitoring means.

The evaluation and monitoring of any manual controls make it possible to ensure an incorporation of the human element that is measurable and monitored.

A performance evaluation mechanism makes it possible to detect and undergo deteriorated working conditions, either by:

Detecting degenerated scenarios and warning of them, for example inadequate light in the room that does not allow the correct operation of the camera and therefore the correct observation.

Operating despite the knowledge of false measurements or suboptimal conditions (the eyes blink, do not focus on the requested place, etc.)

The system is capable of giving information about its capacity to take the measurement successfully or to correct it. It makes it possible to adjust the repetition of the measurement on-demand or as a function of the desired performance.

System Proposed and Main Protocols

The proposed system follows the recommendations above. This system has the purpose of being easy to access, of an affordable price and adapted to the budget of any optician or e-optician.

Composition

The system uses:
a camera, which enables the observation. The technology makes it possible to use simple cameras on the current market and to obtain very precise results.
a computer connected to the Internet, equipment most opticians already have access to. Their practice management software (PMS) often requires them to have such a piece of equipment, in order to be connected with their various suppliers and service providers.
a test object, for certain forms of our product. Depending on the site of use, this test object can vary. For use by Internet for e-opticians, any type of object of known size can be used as a test object such as a simple loyalty or credit card. In stores, clips on the frames will be able to be chosen.

Principle

The system reconstructs the mechanical system of the eyes and measures the PD3D, by observing the face and the focuses of the subject in various configurations. The eye system in 3D is reconstructed, its relationship to the test object, to the face of the user, and to the wearing of the spectacles. On the basis of these items of information, the technology is capable of giving the precise values of the quantities: pupillary distance PD, monoPD and heights. Based on these results, it is possible to add all the measurements and protocols specific to activities and particularities of sight (strabismus etc.) and to describe the visual parameters more precisely with respect to the new measurements useful nowadays for mounting the new-generation lenses.

The computations and interaction can be distributed over the client machine, and remote computation servers, which renders the technology robust to equipment problems and to the local technical context. The updating of the versions and the incorporation of new directives and new protocols is instantaneous because of this.

Finally, the use of video guarantees the capture of a considerable number of images which makes it possible to obtain all the necessary statistics on the quality of the protocol and to propose a reliable measurement.

Associated Protocols

The measurement protocol is short and easy to carry out. It exists with various test objects, but always follows the following principle:

At each point appearing on the screen (up to 3 points for example) (in general from 1 to 50, 1 to 20, preferably 2 to 7), focusing the focus on it, and making a head movement such as slowly turning the head (saying "no") for example.

Figure 7:
FIG. 7 represents photographs of the measurement protocol of the PD with a credit card test object: a) Central point focus; b) Focus on a point on the side of the screen.

This protocol can be carried out in all conditions by using a test object such as for example a card of "credit card" format placed anywhere on the face. FIG. 7 shows an example of the images extracted from a video sequence.

The scenario is as follows:

If the camera is not calibrated, the calibration scenario is carried out.

Figure 3:
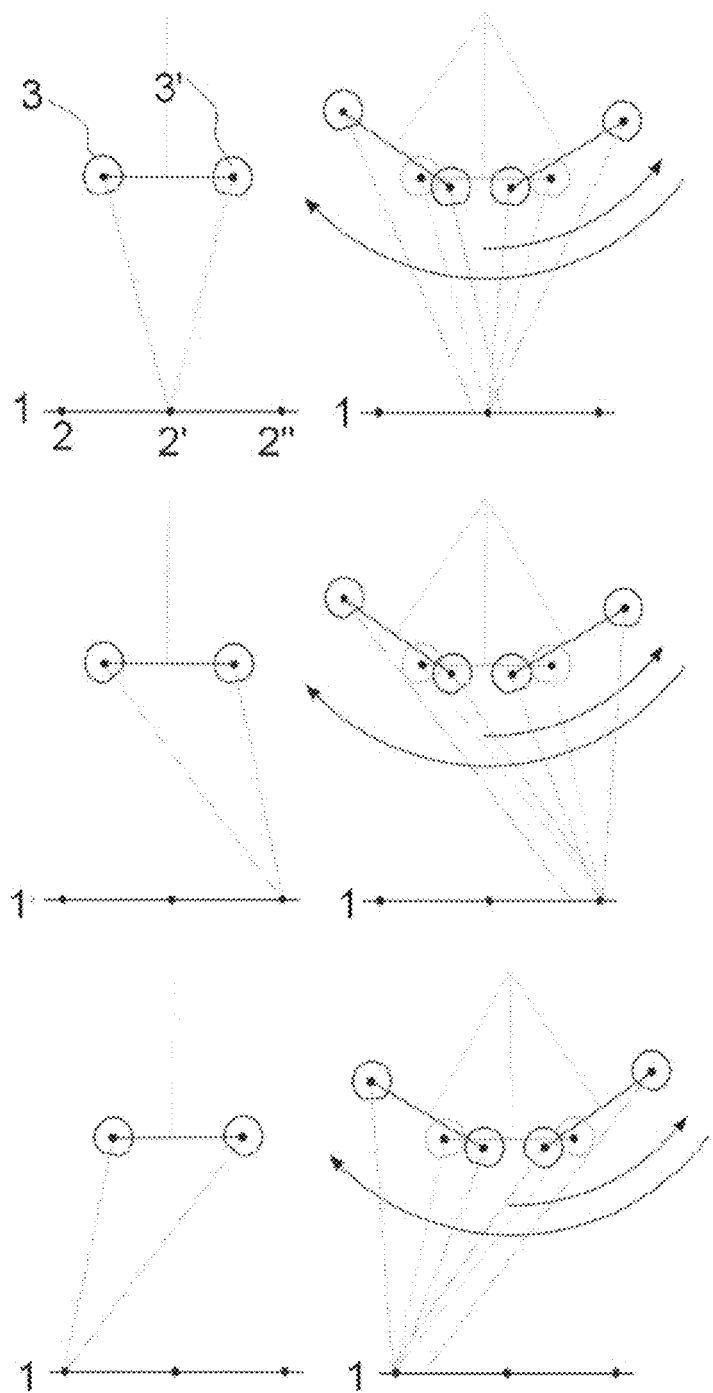
FIG. 3 is a schematic representation of a reconstruction protocol.
Figure 4:
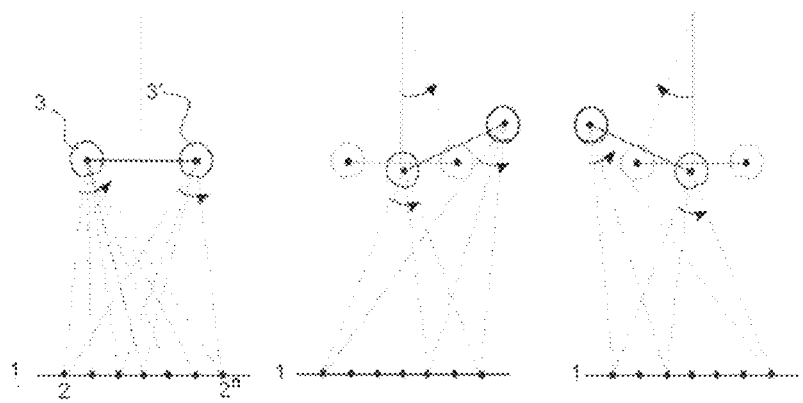
FIG. 4 is a schematic representation of another reconstruction protocol.

The user focuses with his or her eyes (3, 3') at points on a screen (1), and turns his or her head while watching these points (2, 2', 2", 2''') one by one. FIGS. 3 and 4 illustrate implementations of this scenario.

Figure 2:
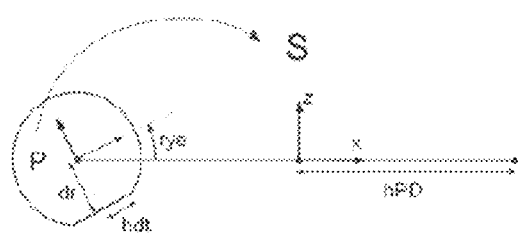
FIG. 2 is a schematic representation of another view of the 3D reconstruction system.

In order to metrically reconstruct the eye system in 3D, it is modeled with the following systems A system Eye: P: hdi, dr, rxe,rye,
A system Eyes: S, hpd, $T_{SM}$, $R_{SM}$.
A system Test object: M, $T_M$, $R_M$.
A system camera: W, K.
A system Screen: 1, and in the following manner (illustrated in FIGS. 1 and 2):
the camera reference frame W defines the origin and the reference frame of the 3D space,
the camera possesses calibration features K making it possible to relate the spatial coordinates of a point in the space with the associated point in the image shot by the camera and displayed on a screen (1),
a set of 3D points, constituting the test object (4), undergo a spatial translation $T_M$ and a rotation $R_M$ in the camera space.

A first point $M_0$ of the set of 3D points of the test object is linked to the eye system at a point (S) in a rigid manner. The rigid transformation linking the test object (4) to the eye system is defined by a translation $T_{SM}$ and a rotation $R_{SM}$ in the space centered on $M_0$. In the camera space the eye system of origin S therefore undergoes the composition of the transformations ($T_{SM}$, $R_{SM}$) and ($T_M$, $R_M$).

The eye system is composed of 2 "eye" systems distant by hpd along the horizontal axis in the reference frame centered on S.

Each "eye" system is modeled by a center of rotation P (S is therefore the barycenter of the points P of each eye), linked at a distance dr to a disc of center I and of radius hdi representing the iris. These discs representing the irises possess 2 degrees of freedom in the system centered on P: 2 rotations rxe and rye corresponding to the movement of rotation from bottom to top of the iris and to the movement of rotation from left to right of the iris in the eye socket respectively.

The transformation ($T_M$, $R_M$) therefore models the translation and the rotation of the movement of the head undergone by the test object M securely fastened to the face. The transformation ($T_{SM}$, $R_{SM}$) models the rigid relation between the centers of rotation of the eyeballs and the test object M (both of them securely fastened to the face). hpd represents half of the desired "PD3D" and dr represents the longitudinal radius of the eyeball. hdi is the radius of the iris. Finally, rxe and rye model the movements of rotation of the eyeballs undergone by the irises.

Variant models can obviously be proposed without harming the resolution (for example modeling the eye as an ellipsoid instead of a segment and a disk).

In this system, only the dimensions of the test object are known with precision. This means that only the positions of the set of points constituting this test object with respect to the first point $M_0$ are known with precision.

Other quantities can be determined statistically such as the average radius of the iris (hdi) or the average longitudinal radius of the human eyeball (dr). The metric reconstruction of the eye system requires finding of the unknown values of the system that are dr, hdi, hpd, $T_{SM}$, $R_{SM}$, $T_M$, $R_M$, rxe for each eye (rxeL and rxeR) and rye for each eye (ryeL and ryeR).

After resolving the unknown values, the eye system is metrically reconstructed according to our model. Thus it is possible to regain independent 3D measurements such as the PD3D of a user (distance between the centers of rotation of the eyes), the sight paths or the 3D measurements as a function of the positioning of a pair of spectacles with respect to the eye system (monoPD, heights, pantoscopic angle etc.).

In order to find the unknown values of the model, it is proposed that a camera be placed on a screen, the user be placed at a distance comprised between about 20 and 40 cm from the camera, and images be acquired via the camera while the user turns his or her head from left to right by focusing at several distinct points spaced by about ten centimeters on the screen. These dimensions guarantee the convergence of the resolution (the important thing being the angle of sight). It is thus possible to thus obtain many series of images in which the user focuses on a fixed point with different rotations of the face. The protocol is shown in FIG. 4.

Two sorts of unknown values can be discerned:
Unknown values with a measurement by image ($T_M$, $R_M$, rxeL, rxeR, ryeL and ryeR).
Unknown values with a global measurement (dr, hdi, hpd, $T_{SM}$, $R_{SM}$).

As indicated above $T_{SM}$, and $R_{SM}$ can be computed by image, if the position of the test object is not considered constant on the surface over the course of the experiment (but securely fastened to the face). For the remainder of the description, these parameters will be considered to have a constant value over the whole experiment: the test object remains securely fastened to the face at the same position and orientation on its surface, with the exception of small variations.

The choice of the resolution method of the system depends on algorithms used for the detection and alignment of the test object, the detection and alignment of the irises, and the evaluation of the performance with in particular the capacity to detect images in which the test object is no longer securely fastened to the face.

In the context where it is possible to detect if the test object is no longer securely fastened to the face, it is possible to resolve the system in two steps:

The first step consists in finding the transformation ($T_M$, $R_M$) undergone by the set of points of the test object in each acquired image. Two methods are possible:

Method 1:

For each image minimization takes place by difference of points (minimization conventionally solved by algorithms of Gauss-Newton type)

The aim is to minimize the following expression:

$$\operatorname{argmin}_{Rm,Tm} \sum_{i=1}^{nPts} [P_{2D}(i) - \operatorname{Proj}(Dp(P_{3D}(i), Rm, Tm)]^2$$

with

Rm, matrix of rotation 3D

Tm, vector translation 3D nPts, number of projected points $P_{3D}$, 3D coordinates of the test object $P_{2D}$, 2D coordinates of the test object in the image (corners, outline points, characteristic points)

Proj, function projecting a 3D point in the image (pinhole camera model)

$$\operatorname{Proj}(P_{3D}) = \begin{bmatrix} x/z \\ y/z \end{bmatrix}$$

where $$\begin{bmatrix} x \\ y \\ z \end{bmatrix} = KM * P_{3D}$$

and KM, calibration matrix of the camera (precision in the calibration part)

$$KM = \begin{bmatrix} fx & suv & u0 \\ 0 & fy & v0 \\ 0 & 0 & 1 \end{bmatrix}$$

$D_p$, function applying the rotation matrix R and the translation vector T to a 3D point for a displacement in 3D $$D_p(P3D) = R*P3D + T.$$

Method 2:

For each image minimization takes place by difference of texture according to the following formula:

$$\operatorname{argmin}_{Rm,Tm} \sum_{i=1}^{nPixels} [Tex(i) - I(W(\operatorname{Proj}(Dp(P_{3D}, Rm, Tm), i))]^2$$

with

Rm, matrix of rotation 3D

Tm, translation vector 3D nPixels, number of pixels composing the texture Tex of the test object I, Image W, function enabling the image to be deformed (I) from 2D image coordinates into Texture (Tex) coordinates Proj, function projecting a 3D point in the image (pinhole camera model)

$D_p$, function applying the rotation matrix R and the translation vector T to a 3D point for a displacement in 3D.

The second step consists in then finding the values of the global variables $T_{SM}$, $R_{SM}$, hdi, hpd as well as the values rxeL, rxeR, ryeL, ryeR for each acquired image. In the same way, two methods are possible:

Method 1:

Over the set of images minimization takes place by difference of points (rxe and rye respectively designate both rxeL, rxeR and ryeL, ryeR) according to the following formula:

$$\operatorname*{argmin}_{\substack{hpd,hdi,dr,\\rxe,rye,\\Rsm,Tsm}} \sum_{i=1}^{nPts} \sum_{j=1}^{nlm} \begin{bmatrix} P_{2D}(i,j) - \\ \operatorname{Proj}(Dp(Dp(P_{3D}(i, hpd, hdi, rxe(j), \\ rye(j)), Rsm, Tsm), Rm(j), Tm(j)) \end{bmatrix}^2$$

with hpd, distance between the center of the eye system and the center of rotation of each eye.

hdi, radius of the disc representing the iris.

rxe, rye, rotations of the irises around the center of the eye (by image).

Rsm, rigid 3D rotation matrix.

Tsm, rigid 3D translation vector

Rm, 3D rotation matrix (by image)

Tm, 3D translation vector (by image)

nPts, number of projected points nlm, number of acquired images $P_{3D}$, 3D coordinates of the outlines of the irises (sampling on the outlines of the discs)

$P_{2D}$, 2D coordinates of the outlines of the irises in the image

Proj, function projecting a 3D point in the image (pinhole camera model)

$D_p$, function applying the rotation matrix R and the translation vector T to a 3D point for a 3D displacement.

Method 2: over the set of images, minimization by texture difference $$\operatorname*{argmin}_{\substack{hpd,dr,hdi,\\rxe,rye,\\Rsm,Tsm}} \sum_{i=1}^{nPix} \sum_{j=1}^{nlm}$$

$$\begin{bmatrix} Tex(i) - \\ I\left(W\left(\operatorname{Proj}\left(Dp\left(\begin{matrix}Dp(P_{3D}(i, hpd, hdi, rxe(j), rye(j)), Rsm, Tsm),\\ Rm(j), Tm(j)\end{matrix}\right)\right)\right)\right) \end{bmatrix}^2$$

with hpd, distance between the center of the eye system and the center of rotation of each eye.

hdi, radius of the disc representing the iris.

rxe, rye, rotations of the irises around the center of the eye (by image).

I, Image

W, function enabling the image to be deformed (I) from 2D image coordinates into Texture (Tex) coordinates Rsm, rigid 3D rotation matrix Tsm, rigid 3D translation vector Rm, 3D rotation matrix (by image)

Tm, 3D translation vector (by image)

nPix, number of pixels composing the texture Tex of the test object nlm, number of acquired images $P_{3D}$, 3D coordinates of the outlines of the irises (sampling on the outlines of the discs)

$P_{2D}$, 2D coordinates of the outlines of the irises in the image

Proj, function projecting a 3D point in the image (pinhole camera model)

$D_p$, function applying the rotation matrix R and the translation vector T to a 3D point for a 3D displacement.

In a first variant of the resolution, in the case where the test object is not continuously securely fastened to the face with the same transformation ($T_{SM}$, $R_{SM}$), the unknown values are distinguished in the following manner:

Unknown values having a measurement by image ($T_M$, $R_M$, $T_{SM}$, $R_{SM}$, rxeL, rxeR, ryeL and ryeR).

Unknown values having a global measurement (dr, hdi, hpd).

The resolution can then be performed by minimizing the following formula:

$$\underset{\substack{hpd, dr, hdi, \\ rxe, rye, \\ Rsm, Tsm, \\ Rm, Tm}}{\operatorname{argmin}} \sum_{i=1}^{nPts} \sum_{j=1}^{nIm} \left[ \begin{array}{c} P_{2D}(i,j) - \\ \operatorname{Proj}(Dp(Dp(P_{3D}(i, hpd, hdi, rxe(j), rye(j)), \\ Rsm(j), Tsm(j)), Rm(j), Tm(j)) \end{array} \right]^2$$

over the set of acquired images.

The minimization is described in terms of difference of points but is also able to be performed in terms of difference of texture.

The resolution in two steps previously described can if necessary be used as an initialization step.

The model makes it possible to solve the various minimizations expressed using conventional algorithms of Gauss-Newton type, the 2D parameters of which are replaced by the 3D parameters of the present invention.

Given that there is only a need for a limited number of images to metrically reconstruct the eye system and that the acquisition of the images can be done in video mode, it is then possible to validate performance using other images of the video. This consists in adding several batches of images to the images necessary for the reconstruction and if necessary in removing certain images in a random manner, to proceed with the reconstruction and to consolidate the results obtained.

A metric reconstruction of the face can be envisioned without a test object securely fastened to the face. It is then proposed to enrich the disclosed model by an angle drye making it possible to explain the fact that the line of sight (straight line passing through the center of the eyeball and the center of the iris) does not pass through the point focused on on the screen but is shifted by an angle drye on the left-right rotation of the eye.

Thus, it is no longer necessary to search for an angle ryeL and ryeR for each image but simply a global dryeL and dryeR: Rye(L or R)=drye(L ou R)+angle present between the horizontal axis and the straight line linking the center of the eyeball and the point focused on on the screen.

Figure 5:
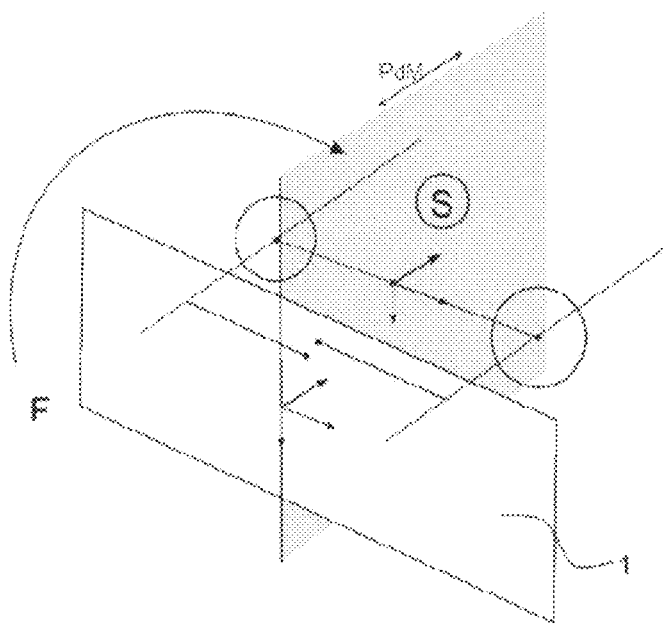
FIG. 5 represents the step of measuring the monoPD.

The reconstruction is then rendered possible by this simplification of the number of parameters and by the fact that the distance between the focus points is known on the screen. The 3D test object securely fastened to the face is then replaced by the points displayed on the screen, the spacing of which is known. The protocol is also enriched by intermediate points as suggested in FIG. 5.

Finally, in all the models envisioned here, the reconstruction of the eye system can if necessary be aided by the reconstruction of characteristic points present on the face. In fact, locating characteristic points of the face in the acquired images can be considered as following and reconstructing points of a 3D test object, the position of which is unknown but which is physically securely fastened to the face.

Implementation

In order to obtain the image indices that enable the described resolution, it is necessary to add processes that enable:

The detection and alignment of the card in all the necessary images,

The calibration of the camera,

The detection and alignment of the irises in all the necessary images,

The evaluation of the performance and the computation of the stability of the result.

For this, the following method is used:

1. Detection and Alignment of the Card

The user presents the card to the camera.

The algorithm automatically detects the card and learns its appearance.

The user puts the card on his or her face, as proposed in the configurations in FIG. 4. For each image needed for the computation of the measurement, the appearance is used to find the card. Then, a precise alignment is carried out and the 3D pose of the card is deduced.

In the case where the camera has to be calibrated, the user presents different configurations of the card to the camera. The card is followed and aligned in each image. The calibration is resolved according to the method of the Calibration section. The calibration and PD shot protocol steps can be merged.

2. Detection and Alignment of the Eyes

For this, a learning model of the eyes is used, learnt under the conditions of the protocol. The eyes are detected then aligned in all the images for which the card has been processed.

3. Monitoring and Performance

The measurement is computed, as well as the 3D pose of all the elements of the system and their relationships. Automatic characterization of the quality of each image and its contribution to the final result is carried out. Among the acquired images, various samples are taken of a certain number of images needed for the reconstruction and for resolving the system again, which makes it possible to deduce therefrom the confidence of the estimate. In the same way one may also evaluate whether the protocol has performed well: the card has not moved on the face during the shot, the eyes have remained sufficiently open, etc.

Alignment Principle

Generally, detection and alignment methods have two opposite types of approach: a so-called "bottom-up" approach, which consists in deducing known structures from a set of characteristics found in the image, and in deducing therefrom transformations or potential candidates for the parameters that are sought, and a so-called "top-down" approach, which uses knowledge about the appearance to search for it in the image. Whether this appearance is the signal image itself or transformed by filters, the support of the sought structure is evaluated on the image to determine the realism of the candidate parameters.

The system according to the invention uses the following alignment principle, which brings together these two approaches and makes the best of both:

At first, the appearance of the sought object is learned. Next probable appearances and positions of this object in the image space under consideration are generated and these representations, called templates, are searched for in the image. These representations can be parameterized or non-parameterized.

Next, the image of the outlines of the image under consideration is created, by a Canny filter for example, and simple geometrical structures are sought that correspond to a parameterized description of the outlines of the possible appearances of the sought object. For the eyes, these are ellipses, for the card, these are an assembly of straight lines and corners.

The solution is chosen that has the best support, and considering the parametric value of the image indices, it is possible to deduce the 3D configurations at the origin of these projections according to the equations presented above. The resolution can be done by robust stochastic method, such as a RANSAC algorithm (Fischler, 1981) and its derivatives (MLESAC, etc.) or by alignment of outlines.

This method is robust to changes in image quality, illumination and occlusions of the object. The step of geometrical alignment is robust to possible errors of scale, of position or of 2D orientation that can be committed by the techniques based on appearance.

This method can include the usual "top-down" or "bottom-up" methods inside the template under consideration to make the tracking more robust. For example, points of interest of Harris type and descriptors of SIFT (Scale-invariant Feature Transform) type or SURF (Speeded Up Robust Feature) type can be used to allow tracking of the attributes of the template (Mikolajcziyk, 2005). An approach is followed similar to that of (Hinterstoisser, 2009), with the difference that the templates and the texture elements are organized and monitored, and that the alignment is geometrical and not based on appearance.

In this method is included its use in multiresolution and in the division into substructures of the template, such as for example the points of interest mentioned above or the division into sub-templates organized spatially.

Card Detection, Tracking and Alignment

For the first detection, the user is asked to place the card in a template presented on the screen. The alignment algorithm is then used.

The texture is then learned by carrying out a transformation of the points of the card of the learning image such that the shape of the texture follow the ratios of the card, by maximizing the covered surface and by minimizing the distortion with respect to the learning image. For this, the homography is searched for that will make it possible to move from found points to a rectangle of max size (height, width among the 4 points under consideration), with max (a,b) a maximum function between two real numbers. The acquired texture is interpolated according to known methods to fill this reference texture denoted CBTex in the remainder of the description.

For subsequent tracking and detections, the texture of the card is searched for in the image by generating a set of templates (the card texture then undergoes a projective 2D transformation), relative to possible 3D poses of the cards.

The deformation of the 2D texture is expressed in the following manner: if R, t is the position of the card in the scene, then the associated homography is expressed H=[R(:, 1:2) t], with R(:, 1:2) the two first columns of the matrix of R. Another means of computing the homography is to compute the projections of the corners of the card on the image under consideration and to deduce the homography between the points of the texture and those of the projection image for the 3D scene parameters under consideration.

The texture CBTex is thus deformed for each template created. For each template, a search in the image is carried out and correlation scores are established. Many methods known to those skilled in the art exist for performing such template matching. These include the correlation known by the name ZNCC (Zero mean Normalized Cross-Correlation) or the alignment of T. Kanade (Baker, 2004), or ESM (Benhimane, 2007).

The template having the best correlation or alignment score is selected from among all the templates produced and tested on the image. As the template is directly associated with a 3D pose, the points on the card are deduced and a geometrical alignment algorithm is carried out if necessary.

For the points found, the best pose that will explain these points is searched for, using the following formula:

$$\mathrm{argmin}_{Pose} \sum_{i=1}^{nPts} [P_{2D}(i) - \mathrm{Proj}(Dp(P_{3D}(i), \mathrm{Pose})]^2$$

Geometrical Alignment of the Card

In order to find the corners of the card precisely without knowing its appearance, its geometrical characteristics are used: the card is described as a series of parameterized curves and straight lines. This is valid for any test object: spectacles, CD, card, face.

The image of the outlines is used, by applying a Canny filter to the original image. The sets of four straight lines that can describe the card are searched for. In order to restrict the possibilities, an initial solution is used: a template when the card is unknown, the solution of the tracking by appearance when the card is known, i.e. the four points associated with the corners of the card.

To find each straight line, a stochastic algorithm (RANSAC (Bolles, 1981), for example) is used, considering the outline points, and an attempt is made to estimate a straight line. The intersections of the straight lines found two by two give the four corner points of the card.

Detection of the Eyes, Tracking and Alignment

For the detection of the eyes, a statistical appearance model is learned of the type known by the acronym AAM (Active Appearance Model) in order to possess an image of the texture of the eyes as well as their variability of appearance.

Probable templates are generated as a function of probable 3D poses for the images under consideration relative to the protocol carried out. It is possible to add the knowledge of the card pose found previously, and to refine the scale of the probable poses for the image under consideration as a function of the card pose.

The templates are first of all the average images of the learnt appearance models. These average templates are aligned by ZNCC correlation, then by alignment algorithm (Inverse Compositional Algorithm for example (Baker, 2004)) enabling the whole model of shape and appearance to vary.

This process is repeated for the set of images under consideration and followed by an alignment.

Geometrical Alignment of the Eyes

Once the initial position and scale of the template are given by the previous alignment, the image of the outlines is used and ellipses, image supports of the irises, are searched for in the zone under consideration. There again, a stochastic algorithm of sampling points and evaluation of the 2D support of the ellipse structure such as RANSAC is used. This makes it possible to find the image index in spite of the many problems of reflections on the cornea, or of blinking of the eyes, which imply a great and unpredictable change of appearance.

Test Objects, Calibration and Metrics

Calibration of the Camera

The calibration consists in finding the intrinsic characteristics of the camera according to the following matrix:

$$\begin{bmatrix} fx & suv & u0 \\ 0 & fy & v0 \\ 0 & 0 & 1 \end{bmatrix}$$

with:

fx and fy, the focal distances in pixel width and height (fx and fy can if necessary be considered equal to a value f), (u0, v0), the coordinates of the optical center projected in the image (u0 and v0 can be considered if necessary at the center of the image), and SUV a factor expressing the non-orthogonality of the camera (generally considered as zero).

The calibration makes it possible to link the spatial coordinates of a point in space with the associated point in the image shot by the camera. It is made from images of a 3D test object in various rotations and positions. The calibration is conventionally resolved using non-planar or heavily textured planar test objects.

Two approaches are proposed.

Approach 3D 1: for the set of acquired images, minimization by difference on points (conventional resolution using least square Gauss-Newton algorithms)

$$\operatorname{argmin}_{K,Rm,Tm} \sum_{i=1}^{nPts} \sum_{j=1}^{nlm} [P_{2D}(i,j) - \operatorname{Proj}(Dp(P_{3D}(i), Rm(j), Tm(j), K)]^2$$

with

K, the vector grouping the features of the camera (focal length f, coordinates u0, v0 of the optical center in the image)

Rm, 3D rotation matrix of the test object (by image)

Tm, 3D translation vector of the test object (by image)

nPts, number of projected points nlm, number of acquired images $P_{3D}$, 3D coordinates of the test object $P_{2D}$, 2D coordinates of the test object in the image (corners, outline points, characteristic points)

Proj, function projecting a 3D point in the image (pinhole camera model)

$$\operatorname{Proj}(P_{3D}) = \begin{bmatrix} x/z \\ y/z \end{bmatrix}$$

where $$\begin{bmatrix} x \\ y \\ z \end{bmatrix} = KM * P_{3D}$$

and KM is the calibration matrix of the camera $$KM = \begin{bmatrix} fx & suv & u0 \\ 0 & fy & v0 \\ 0 & 0 & 1 \end{bmatrix}$$

$D_p$, function applying the rotation matrix R and the translation vector T to a 3D point for a displacement in 3D $$D_p(P3\ D) = R*P3D + T.$$

Approach 3D 2: for the set of acquired images, minimization by difference on textures $$\operatorname{argmin}_{Rm,Tm,K} \sum_{i=1}^{nPix} \sum_{j=1}^{nlm} [Tex(i, j) - I(W(\operatorname{Proj}(Dp(P_{3D}, Rm(j), Tm(j), K), i))]^2$$

with

Rm, 3D rotation matrix (by image)

Tm, 3D translation vector (by image)

nPix, number of pixels composing the texture Tex of the test object

I, Image

W, function enabling the image (I) to be deformed from 2D image coordinates into the Texture (Tex) coordinates Proj, function projecting a 3D point in the image (pinhole camera model)

$D_p$, function applying the rotation matrix R and the translation vector T to a 3D point for a displacement in 3D.

The model makes it possible to resolve these various minimizations using conventional methods of Gauss-Newton type, the 2D parameters of which are replaced by our 3D parameters.

An initialization of K can be obtained using the homographies relating in each image the metric coordinates of the 3D plane of the test object to the image coordinates (Maybank, 1999) and (Zhang, 2000).

Types of Test Object

Any object of initially known size and which can be securely fastened to the face can serve as test object, such as for example a bank card, a loyalty card with a bank card format, a CD (compact disc), a pair of spectacles of known dimensions, or again a known object held rigidly to a pair of spectacles.

A model of the reconstruction of the eye system even makes it possible to do without a test object securely fastened to the face. In this precise case, the test object in question is composed of points displayed on the screen, the distance between the points of which is known.

Finally, the face can be used as a test object if its 3D dimensions are known. These dimensions can be reconstructed using the card and the reconstruction of points of the face, or the use of statistic face models (Vetter, 2005), the metric being contributed by our method of resolution and the initial test object under consideration.

Geometrical Calibration of the Screen

In order to guarantee the distance of separation of the points sighted by the user, and to adapt it where applicable, it is necessary to measure its screen in a metric space. The system can then propose adequate points of sight with the size of the screen and thus adapt the distance of the user for the successful accomplishment of the protocol.

Figure 8:
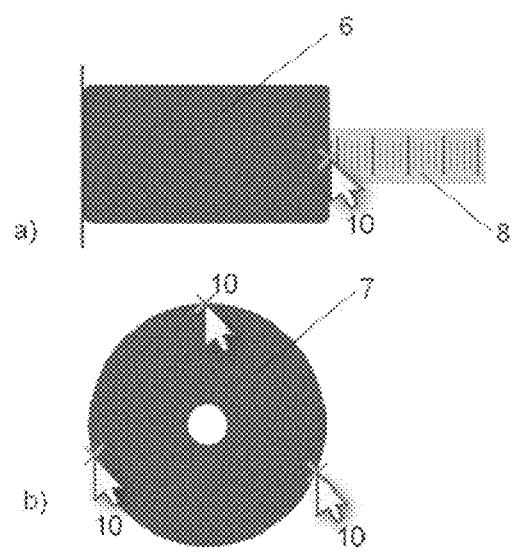
FIG. 8 represents the card a) and the CD b) used during calibration of the screen.

In the case where the test object is a planar object, such as a Compact Disc or a credit card, the system asks him or her to place the object against the screen. It then displays a grid, and the user clicks on the edges of the object. The resolution of the native screen being known by the program via the display management system, a simple scale factor is applied to find the real dimensions of the tablet, in an imperfect but sufficiently precise manner to position the points of sight with less than 5 mm of error. FIG. 8 gives an example of a grid template for a credit card (6) a) or a CD (7) b), and the points (10) of the minimum clicks to be made by the user. The reference frame 8 represents an element of measurement of the metric space.

PV Measurements in Single-Camera Context

Definitions of 3D PV Measurements

For PV measurements, several ways of redefining them exist, and the system is capable of measuring them all.

Definitions are given of the most probable concepts arising from conventional definitions, which are considered in a 2D context, in the sense that the proposed measurements must be performed in a given and observed position with an orthographic projection.

An initial registration is considered according to a rotation Tx around the x-axis of the reference frame Eyes (S) with respect to a photo such that the person is carrying his or her head and spectacles in a natural position. The 3D definition can become independent of the focus, and can make it possible to adapt the edging of the lenses as a function of each distance that it may be desirable to explicitly consider, because the 3D expression of these concepts makes it possible to compute the points of intersection of the supposed focus with the plane of the mounted lens.

To enable 3D PV measurements, it is considered that the frame is placed on the face, and that the transformation between the reference frames of the frames (F) and the eye system (S) is computed. It is possible to be remove it or to consider it in the computation as a function of the desired mounting of the lenses.

For left and right 3D monoPDs, two definitions are considered. The first is to measure the orthogonal distance between the vertical plane of symmetry of the frame (PdM) (plane yz in the frame's frame of reference) and the position of the center P of each eyeball, as illustrated in the figures. A second possible measurement is to compute the points of intersection between the line of sight 3D of each eye and the plane of the lens, for a considered focus (in general at infinity, but our 3D proposition makes it possible to determine each focus under consideration more precisely if necessary). The sought-after measurement is then the distance between the vertical plane and the points of intersection.

Figure 6:
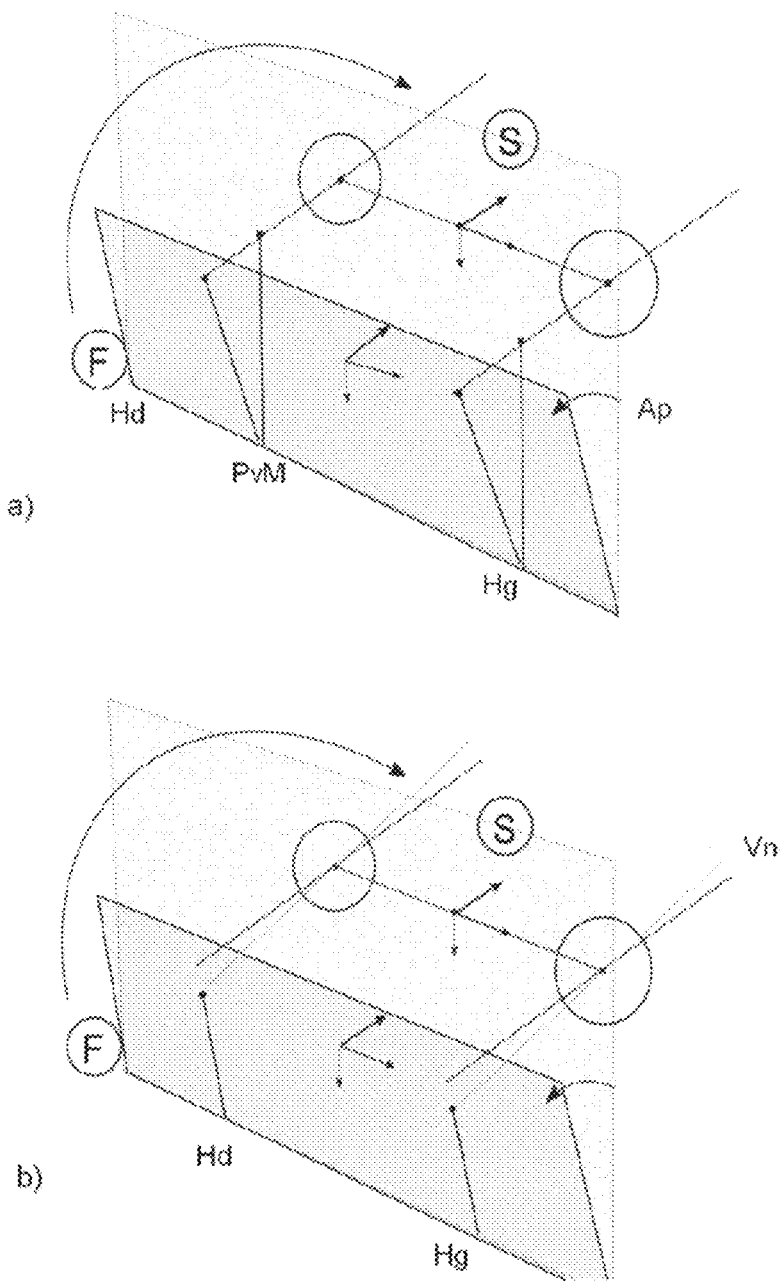
FIG. 6 represents the two variants of the step of measuring the height.

For the heights (right heights :HD, left heights :Hg), the orthogonal distance is measured between the horizontal plane passing through the eye and the straight line passing through the bottom point of the frame at the level of the lens (PvM), as illustrated in FIG. 6. This straight line is situated at the bottom point of the inner bezel. Two measurements are then possible: distance in the plane of the lens, or distance in the vertical plane of the spectacles' reference frame perpendicular to the horizontal eye plane, since the frames of reference of the eye and the spectacles have been registered beforehand.

A variant consists, as for the monoPD (mPD), in computing the points of intersection between the radii of sight (Vn) and the planes of the spectacles that we have just described, as indicated in the bottom of FIG. 6. The computation of the distance in the vertical plane corresponds to the 3D representation of the usual definition of the heights.

Pantoscopic angle (Ap): with respect to the natural position of the face under consideration in our definitions, the pantoscopic angle measures the angle between the plane of inclination of the lenses and the registered reference frame of the face in the natural position.

Measurements with Wearing of Real Frames

The PV measurements require the frames to be worn. They are deduced in 3D by locating the 3D points and lines enabling their measurements. If the frame is unknown to the system (no 3D model available), the necessary 3D points and curves are reconstructed. For this, the image indices are located and aligned by the texture then geometrical alignment method proposed in the section on the alignment principle. If the frame is known, it can constitute a test object. It is either fabricated explicitly for the measurement or it is a spectacle of which the 3D model is obtained by manual design or automatic reconstruction.

Unknown Frame

For an unknown frame, images are taken of the frame worn by the user. The resolution of the PD having been carried out, the 3D planes and straight lines are regained by their projections in the images. For the plane of symmetry of the monoPD, the support surface perpendicular to this plane is searched for, such that the projection in the images allows the symmetry of the appearance of the spectacle in the space of the support surface, as shown in the following equations:

$$\text{argmin}_{\gamma, Rp, Tp} \sum_{i=1}^{nPix} f_s(i, I(W(\gamma, Rp, Tp)))^2$$

with

Rp, 3D rotation matrix of the support plane

Tp, 3D translation vector of the support plane nPix, number of pixels composing half of the texture of the pair of spectacles (without the lens part)

I, Image

W, function making it possible to form the image (I) from a support of curvature y, and of pose ($R_p, T_p$).

$f_s$, symmetry function: $f_s(i, \text{Image}) = \text{Image}(i) - \text{Image}(i\_\text{symetrique})$.

For the 3D straight line passing through the bottom of the frame, it is computed from several images by the intersection of the planes passing through the optical center and the 2D straight lines referenced in the images, which can be determined by clicks of the user or by a texture and alignment search on a knowledge base of learnt spectacles (detection and alignment of statistical models).

For the inclination of the plane of the lenses, it is enough to find the straight line of the upper bezel of the frames as indicated above, and to compute the angle between the reference frame of the eyes and the inclination of the plane that contains these two 3D straight lines.

To better compute the points of intersection of the focus and of the lens (if the associated definitions are chosen) it is possible to introduce the a priori knowledge of the shape of the lens surface.

Frame of Known Model

For a known 3D model, the necessary points are already referenced on the model. This can be done by manual or automatic method, according to methods of 3D analysis of surface and appearance.

The problem that occurs is then the search for the pose parameters of the 3D model in the scene, such that the errors of reprojection of the shape of the frame are minimized in the images under consideration. It is possible to use a geometrical solution or to use the appearance as an aid if that is available. Conventional registration techniques such as (Vetter, 2005) can be used, by taking for the initial solution the pose of the eye system S translated by −12 mm along z, this figure being the average lens-eye distance expected when wearing spectacles.

Measurements with Wearing of Virtual Frames

If a fine reconstruction of the 3D face of the user is available, then the positioning is done by simulation of the wearing of the spectacle on the face. A manual 3D adjustment is proposed that follows the physical constraints of the face and of the frame.

If a sufficiently precise 3D model is not available, an operator or the user himself or herself adjusts the pair in 3D in a visualization interface.

The virtual adjustment and its interface are described here:

The tool shows several acquired views of the user that allow good visualization of the adjustment, as well as a real-time view of the video stream. The user manipulates a 3D monitor view which enables the pair to be displaced with authorized degrees of freedom: opening of arms, rotation, etc. If the 3D face is known, these movements are constrained by the points of contact of the 3D surfaces of the face and the spectacles.

When the pair is manipulated in 3D, its projection is carried out over the set of static and dynamic real views in augmented reality. The user can thus propose various natural head carriages for various activities and adjust their spectacles accordingly. The 3D measurements needed for the mounting are then stored and analyzed by a professional.

This tool is used by the end user for the shot and the head carriage, and by the optics professional for the choice of views and measurements for the adjustment of the frames and the mounting of the lenses. These two users can both be present at the moment of the virtual try-on or the method can be accomplished at two times or in two places if the optician is not in the same physical place or in the same shot time. Indeed, the acquired images can be replayed and readjusted for the professional later or from another place in real time. This enables remote processing or the taking of measurements online assisted by a professional.

This tool also allows the user to define their lens needs without the inconvenience of trying them on.

Other Characteristics of the System

Architecture

The method uses a Client-Server architecture which makes it possible to remove the computations, videos and images acquired and to distribute the interfaces of adjustment for the various users.

Analysis of Ocular Behavior

The method makes it possible to reconstruct the ocular system and to find the sights performed for each acquired image. Knowing the metric distances between the points sighted in the screen system E, it is possible to define a model of convergence for all the acquired positions and interpolate this model for other sighted points.

Thus a calibration of the ocular system is proposed, presenting the user with a matrix of points that covers his or her screen. During a tracking of the focus, one is in a position to deduce what points on the screen are focused at by the user in real time.

The method described functions just as well, and is simplified, when two cameras are available instead of a single one connected by a known or unknown rigid stress. Similarly, the use of devices giving depth is compatible with the equations and the system described in the present invention and add to the stability or immediacy of the result.

The system according to the invention can be used for various applications, the main ones of which are as follows:

Online SV measurements: A loyalty card or a CD can be used to perform the protocol. Certain media with integrated cameras, nowadays very widespread, facilitate the performance.

In-store SV measurements: The test object can be a specially manufactured card, a CD, but also test objects that hook onto real frames. In certain cases, the real frame chosen becomes the test object and the clip-on objects are not necessary.

In-store PV measurements: Since traditional PV measurements have to be carried out while wearing the frame for a given focus and face position, the frame is needed. The test object-frame solution meets this need automatically. The use of a more simple test object, such as the card, is possible, in a mode of semi-assistance by the optician: the latter then gives the system a few indices on images. This operation is evaluated in real time by the performance control system.

Online PV measurement: The frame not being available online for PV measurements, the virtual try-on technology is involved in the measurement process. It enables the wearing of the frame to be simulated and the expected PV measurements to thus be taken. As in real wearing conditions (more comfortably, even, because the user can see himself or herself keeping his or her own spectacles during the virtual try-on) the user observes himself or herself in the screen (mirror), and can see him or herself from several points of view.

The PV measurements are carried out in 3D and for as many configurations of sight as desired. The e-optician can if necessary assist with and monitor this taking of measurements.

EXAMPLES

Example of PD measurements

| PD Measurement | FittingBox Perfect Fit | Pupillometer |
|---|---|---|
| Precision | +−0.2 mm | +−0.25 mm |
| Stability | +−1 mm | +−1 mm |
| Repeatability | 1 measurement (5 integrated unit verifications) | 3 to 5 measurements needed. |
| Final precision in real conditions | +−0.2 mm | +−1 mm |

Example of PV Measurement

| | monoPD | Heights |
|---|---|---|
| PV Measurement precision in-store | +−0.75 mm | +−0.75 mm |
| PV Measurement precision online | +−1 mm | +−1 mm |

The invention claimed is:

1. A method for determining ocular and optical measurements for fabricating and mounting lenses of corrective spectacles for a user, comprising the steps of:

determining a template and a size of a test object selected from a list of standardized objects comprising a bank card, a loyalty card with a bank card format, a compact disc (CD) and a pair of spectacles;

receiving images of a face of the user from a camera, the images comprising the test object;
detecting the test object in the images;
determining a set of 3D points constituting the test object;
calibrating the dimensions of the images by aligning the template to the detected test object; and
determining an interpupillary distance (PD3D) between user's two eyes by a processor configured to: model an eye system of the user, using a protocol of three-dimensional reconstruction of the eye system, the reconstructed eye system including a tridimensional model of each eye positioned in a tridimensional space; and measure the interpupillary distance (PD3D) between user's two eyes reconstructed in three dimensions, the interpupillary distance defining a distance between rotation centers of two eyes.

2. The method as claimed in claim 1, further comprising the step of performing the ocular and optical measurements for a plurality of points of sight and a plurality of orientations of the face of the user.

3. The method as claimed in claim 2, further comprising the step of modeling the eye system of the user from the following ocular and optical measurements of the user's eyes: a size of an iris, a size of eyeballs, an orientation of the eyeballs in their socket, and a pose of a set of two eyes in a reference frame of the camera.

4. The method as claimed in claim 1, further comprising the step of measuring a monopupillary distance (monoPD), heights and a pantoscopic angle, directly in a three-dimensional system of a reconstructed eye of the user.

5. The method as claimed in claim 1, further comprising the step of aligning image indices using an alignment principle of combining a bottom-up approach and a top-down approach, the bottom-up approach comprises deducing known structures from a set of characteristics found in the image and deducing therefrom transformations or potential candidates for parameters that are sought, and the top-down approach utilizes knowledge about an appearance to search for it in the image.

6. The method as claimed in claim 1, further comprising the step of utilizing one or more test objects securely fastened or in proximity to the face of the user.

7. The method as claimed in claim 6, wherein the test object is in a shape of a rectangular card.

8. The method as claimed in claim 6, wherein the test object is contained in a visualization screen.

9. The method as claimed in claim 8, further comprising the step of determining a size of the visualization screen using a planar object.

10. The method as claimed in claim 6, further comprising the step of utilizing the object at the start of the protocol.

11. The method as claimed in claim 1, wherein the face of the user acts as a test object for the eye system.

12. The method as claimed in claim 1, further comprising the step of obtaining progressive vision measurements corresponding to fabrication and mounting of lenses correcting different types of defects on different points of their surface using a virtual try-on of three-dimensional spectacles.

13. The method as claimed in claim 1, further comprising the step of calibrating the camera.

14. The method as claimed in claim 8, further comprising the step of geometrically calibrating the visualization screen.

15. The method as claimed in claim 1, further comprising the step of evaluating stability and performance of the three dimensional eye system to detect and correct production defects in the lenses.

16. The method as claimed in claim 1, further comprising the step of interactively performing the steps of receiving and modeling in real time.

17. The method as claimed in claim 1, further comprising the step of automatically modeling the eye system without an assistance of an operator.

18. The method as claimed in claim 1, further comprising the step of analyzing an ocular behavior, wherein the user is presented with a matrix of points that covers a screen of the user, and, during a tracking of a focus, points on the screen focused at by the user in real time are deduced.

19. The method as claimed in claim 1, wherein a client-server architecture is utilized such that the step of receiving images are performed by a client machine and the step of modeling is performed by a computation server.

20. The method as claimed in claim 1, further comprising the step of operating two cameras connected by a rigid stress.

21. The method as claimed in claim 1, further comprising the step of measuring depth using at least one depth device.

* * * * *